US012180447B2

(12) United States Patent
Chou et al.

(10) Patent No.: US 12,180,447 B2
(45) Date of Patent: Dec. 31, 2024

(54) BONE MARROW MICROFLUIDIC DEVICES AND METHODS FOR PREPARING AND USING THE SAME

(71) Applicants: President and Fellows of Harvard College, Cambridge, MA (US); The General Hospital Corporation, Boston, MA (US)

(72) Inventors: David Benson Chou, Boston, MA (US); Liliana S. Teixeira Moreira Leijten, Maastricht (NL); Arianna Rech, Leicestershire (GB); Richard Novak, Jamaica Plain, MA (US); Donald E. Ingber, Boston, MA (US); Yuka Milton, Cambridge, MA (US); Viktoras Frismantas, Roxburg Crossing, MA (US); Oren Levy, Brookline, MA (US)

(73) Assignees: President and Fellows of Harvard College, Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 18/343,514

(22) Filed: Jun. 28, 2023

(65) Prior Publication Data
US 2023/0357690 A1 Nov. 9, 2023

Related U.S. Application Data

(63) Continuation of application No. 16/496,997, filed as application No. PCT/US2018/024377 on Mar. 26, 2018, now Pat. No. 11,845,920.
(Continued)

(51) Int. Cl.
C12M 3/06 (2006.01)
B01L 3/00 (2006.01)
(Continued)

(52) U.S. Cl.
CPC ....... *C12M 23/16* (2013.01); *B01L 3/502715* (2013.01); *C12M 25/02* (2013.01);
(Continued)

(58) Field of Classification Search
None
See application file for complete search history.

(56) References Cited

U.S. PATENT DOCUMENTS

| 8,647,861 B2 | 2/2014 | Ingber |
| 2003/0087290 A1 | 5/2003 | Tarlov |

(Continued)

FOREIGN PATENT DOCUMENTS

| WO | 2012/166903 | 12/2012 |
| WO | 2013/086486 | 6/2013 |

(Continued)

OTHER PUBLICATIONS

International Search Report and Written Opinion of International Searching Authority for International Patent Application No. PCT/US2018/024377, mailed Jun. 7, 2018 (8 pages).
(Continued)

Primary Examiner — David W Berke-Schlessel
(74) Attorney, Agent, or Firm — Nixon Peabody LLP

(57) ABSTRACT

The present disclosure relates to a microfluidic devices and methods for culturing bone marrow cells. Aspects include methods of preparing microfluidic devices and culturing bone marrow cells with the microfluidic devices. In some aspects, a method includes providing a microfluidic device having an upper chamber, a lower chamber, and a porous membrane separating the upper chamber from the lower
(Continued)

chamber. The method further includes seeding walls of the lower chamber and a bottom surface of the membrane with endothelial cells. The method further includes providing a matrix within the upper chamber. The matrix includes fibrin gel and bone marrow cells. The method further includes filling or perfusing the upper chamber with a media.

8 Claims, 11 Drawing Sheets

Related U.S. Application Data

(60) Provisional application No. 62/476,205, filed on Mar. 24, 2017.

(51) Int. Cl.
 *C12M 1/00*    (2006.01)
 *C12M 1/12*    (2006.01)
 *C12N 5/077*    (2010.01)
 *G01N 33/50*    (2006.01)

(52) U.S. Cl.
 CPC ........... *C12M 29/10* (2013.01); *C12N 5/0669* (2013.01); *G01N 33/5008* (2013.01); *B01L 2300/12* (2013.01); *C12N 2501/40* (2013.01); *C12N 2501/999* (2013.01); *C12N 2502/28* (2013.01); *C12N 2533/54* (2013.01); *C12N 2533/56* (2013.01); *C12N 2533/90* (2013.01)

(56) References Cited

U.S. PATENT DOCUMENTS

| | | |
|---|---|---|
| 2011/0287978 A1 | 11/2011 | Lee |
| 2016/0046897 A1 | 2/2016 | Ingber |
| 2016/0097033 A1 | 4/2016 | Lopez |

FOREIGN PATENT DOCUMENTS

| | | |
|---|---|---|
| WO | 2013/086502 | 6/2013 |
| WO | 2015/138032 | 9/2015 |
| WO | 2016/010861 | 1/2016 |

OTHER PUBLICATIONS

Partial Supplemental European Search Report for European U.S. Appl. No. 18/771,902, mailed Mar. 31, 2021 (12 pages).
Extended European Search Report for European Patent Application No. 18771902, mailed Jul. 7, 2021 (11 pages).
Torisawa et al., "Bone Marrow-on-a-Chip Replicates Hematopoietic Niche Physiology in Vitro," Nature Methods 11, No. 6: 663-669 (2014) (31 pages).
Search Report and Written Opinion for Singapore Patent Application No. 11201908541S, mailed Dec. 7, 2022 (13 pages).
Written Opinion for Singapore Patent Application No. 11201908541S, dated Jul. 21, 2022 (6 pages).
Mahadik, et al., "High-throughput analysis of single hematopoietic stem cell proliferation in microfluidic cell culture arrays," Advanced Healthcare Materials, 3, 449-458, 2014.
Guy, et al., "Fibrin gel formation in a shear flow," Mathematical Medicine and Biology, 24, 111-130, 2005.
Li, et al., "Hematopoietic stem cell repopulating ability can be maintained in vitro by some primary endothelial cells," Experimental Hematology, 32, 1226-1237, 2004.
Mohle, et al., "The Role of Endothelium in the Regulation of Hematopoietic Stem Cell Migration," Stem Cells, 16, 159-165, 1998.
Toh et al.; "A novel 3D mammalian cell perfusion-culture system in microfluidic channels"; Lab Chip, 2007, 7, pp. 302-309 (8 pages).
Torisawa et al.; "Modeling Hematopoiesis and Responses to Radiation Countermeasures in a Bone Marrow-on-a-Chip"; Tissue Engineering: Part C, vol. 22, No. 5, pp. 309-515; 2016 (7 pages).
Third Written Opinion issued in Singapore Application No. 11201908541S, dated Jul. 3, 2023 (6 pages).

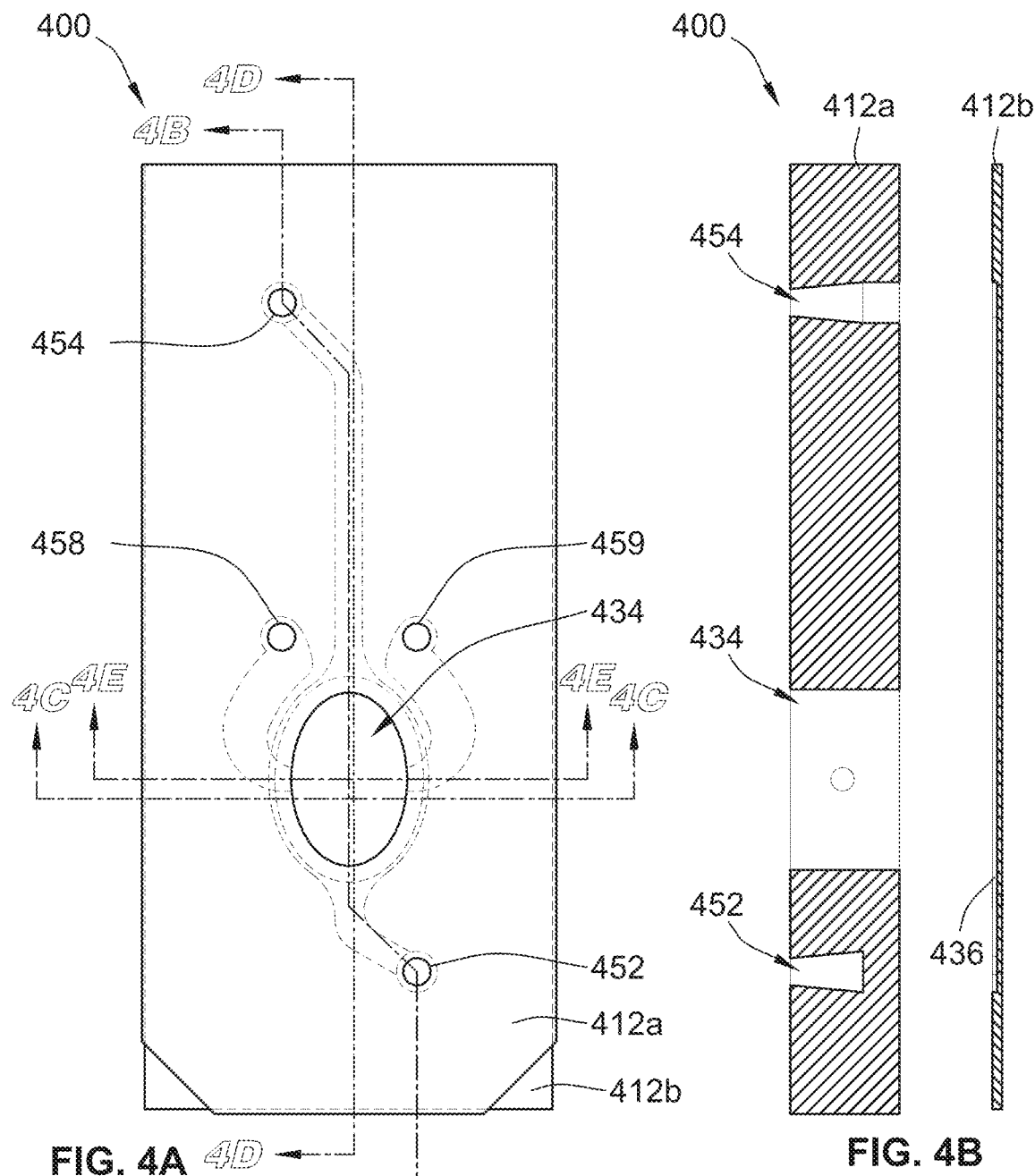
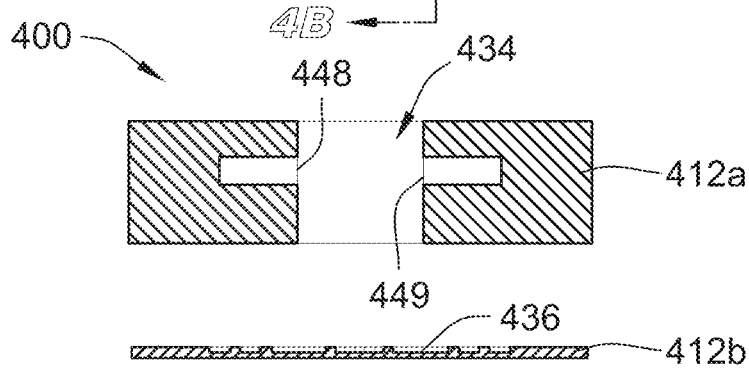

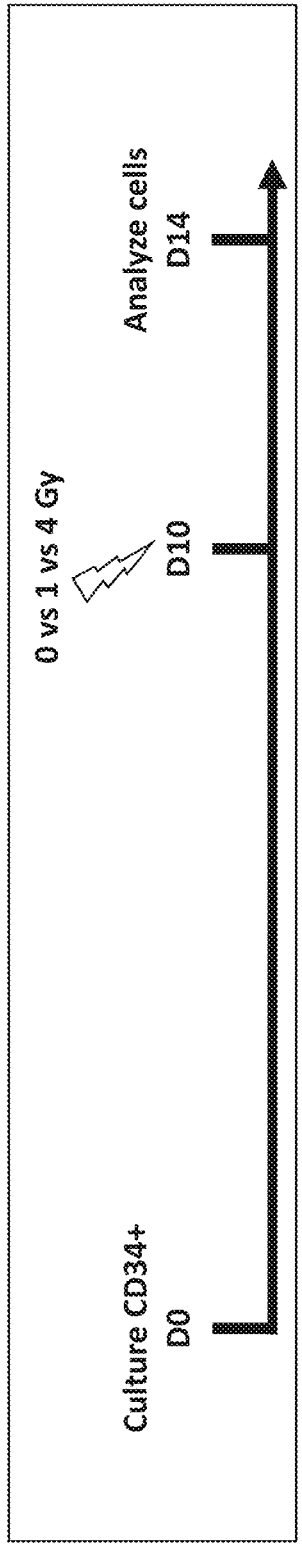
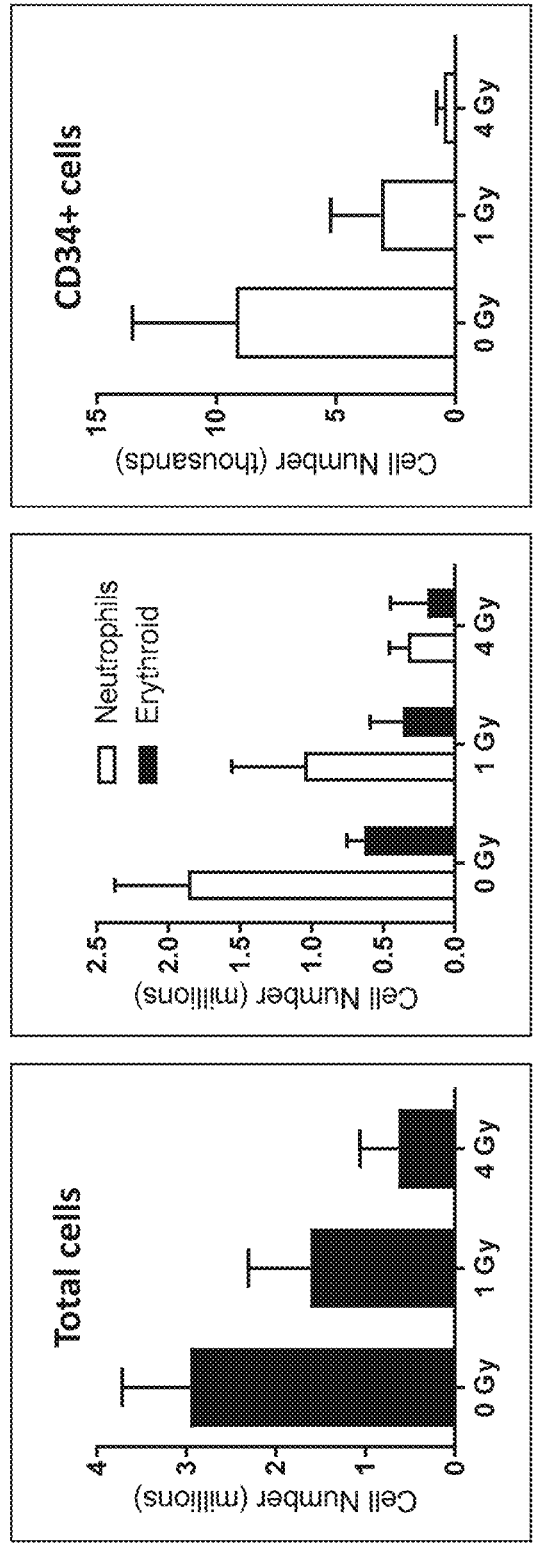

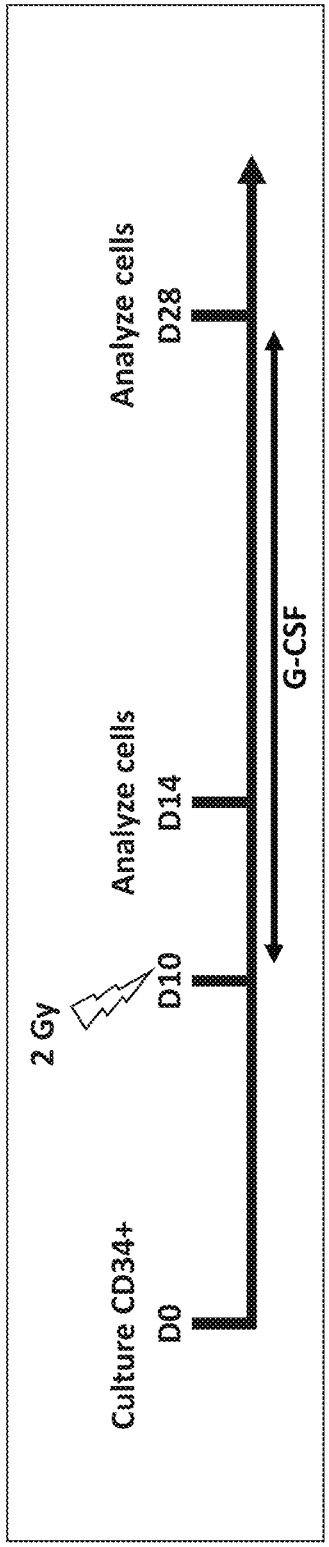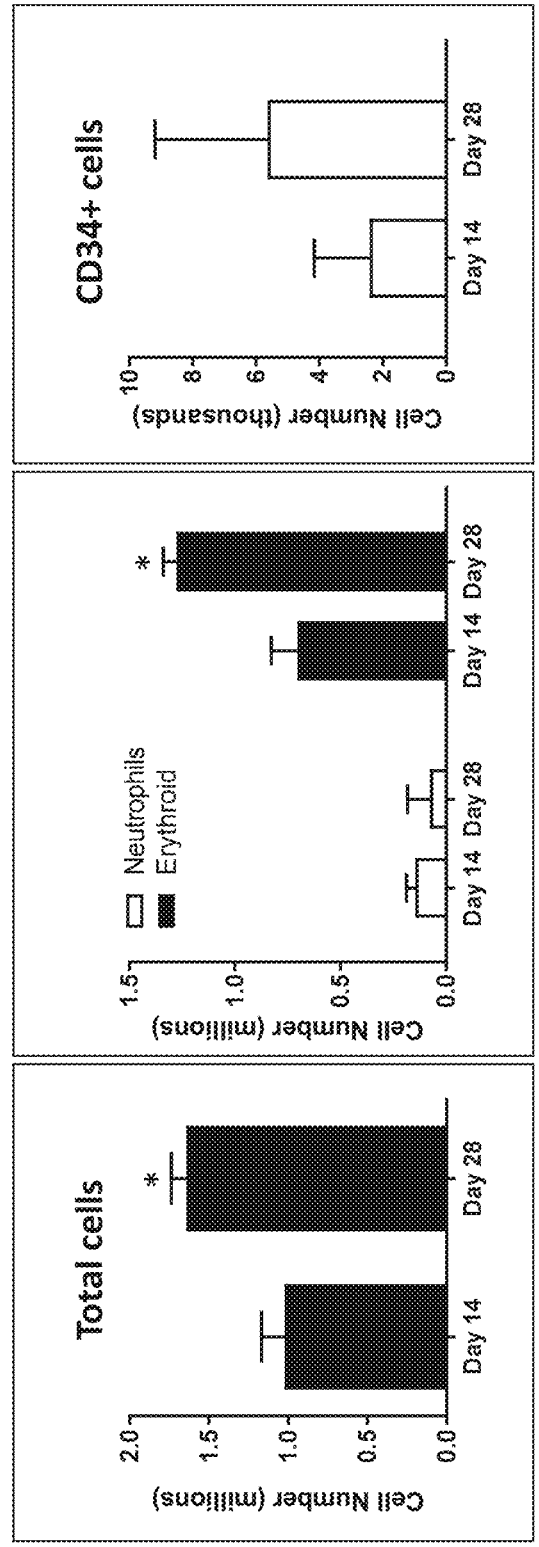
FIG. 9A
FIG. 9B
FIG. 9C
FIG. 9D

BONE MARROW MICROFLUIDIC DEVICES AND METHODS FOR PREPARING AND USING THE SAME

CROSS-REFERENCE TO RELATED APPLICATIONS

This application is a continuation of U.S. application Ser. No. 16/496,997, filed Sep. 24, 2019, now allowed, which is a National Stage Entry of PCT/US2018/024377, filed Mar. 26, 2018, which claims benefit under 35 U.S.C. § 119(e) of U.S. Provisional Application No. 62/476,205, filed Mar. 24, 2017, the contents of each of which are incorporated herein by reference in their entirety.

GOVERNMENT SUPPORT

This invention was made with government support under grant no. 5T32CA009216-35 awarded by the National Institutes for Health (NIH), grant no. W911NF-12-2-0036 awarded by the Defense Advanced Research Projects Agency (DARPA), and grant no. HHSF223201310079C awarded by the U.S. Food and Drug Administration (FDA). The government has certain rights in the invention.

FIELD OF THE INVENTION

The present disclosure relates generally to microfluidic devices and, more particularly, to microfluidic devices and methods of use for culturing bone marrow cells.

BACKGROUND

Microfluidic devices exist that allow for the in vitro mimicking of biological conditions in vivo. Such microfluidic devices have a membrane that separates two microchannels, where cells, particulates, and other matter can communicate through the membrane. The microchannels allow for the flow of fluid, optionally including cells, particulates, and other matter, past the membrane. However, not all biological systems reduce to the system of two microchannels separated by a membrane. Further, the culturing required to mimic biological systems in vivo cannot all relay on a system of two microchannels separated by a membrane. Accordingly, the present disclosure solves these and other problems associated with microfluidic devices and the ability to mimic biological systems.

SUMMARY OF THE INVENTION

Aspects of the present disclosure include microfluidic devices and associated methods for culturing bone marrow cells.

In a first aspect of the disclosure, a method of preparing a bone marrow microfluidic device is disclosed. The method includes providing a microfluidic device having an upper chamber, a lower chamber, and a porous membrane separating the upper chamber from the lower chamber. The method also includes providing a matrix within the upper chamber. The matrix can include bone marrow cells. The method further includes perfusing a first media through the lower chamber. The method further includes filling a remainder of the upper chamber with a second media.

The first aspect can include any one or more of the foregoing aspects, each alone or in any combination. In one aspect, the second media can be a hematopoietic media. In one aspect, the hematopoietic media can be a serum-free expansion medium, fetal bovine serum, cytokines, erythropoietins, a granulocyte colony-stimulating factor, aprotinin, or a combination thereof. In one aspect, the first media can be endothelial media. In one aspect, the endothelial media can include endothelial cell growth media. In one aspect, the endothelial cell growth media can include human microvascular endothelial cells, bovine microvascular cells, fetal bovine serum, or a combination thereof. In one aspect, the matrix can be an extracellular matrix. In one aspect, the extracellular matrix can be fibrin gel. In one aspect, the fibrin gel can include fibrinogen, collagen, aprotinin, thrombin, or a combination thereof. In one aspect, the matrix can be a laminin-containing gel. In one aspect, the laminin-containing gel can be Matrigel. In one aspect, the matrix can be collagen gel. In one aspect, the bone marrow cells can include stromal cells. In one aspect, the bone marrow cells can include bone marrow progenitor cells. In one aspect, the bone marrow progenitor cells can be CD34+ bone marrow progenitor cells. In one aspect, the method further includes seeding walls of the lower chamber and a bottom surface of the membrane with endothelial cells. In one aspect, the endothelial cells can be human umbilical vein endothelial cells. In one aspect, the endothelial cells can be human bone marrow endothelial cells. In one aspect, the method can include coating the bottom chamber with fibronectin, collagen, or a combination thereof prior to seeding the first cells. In one aspect, the collagen can be collagen type I. In one aspect, the method can include flowing a solution of the fibronectin and the collagen through bottom chamber for about one hour to coat the bottom chamber. In one aspect, the concentration of the fibronectin in the solution can be about 100 μg/mL and the concentration of the collagen can be about 50 μg/mL. In one aspect, the method can include rinsing the bottom chamber with water after the coating. In one aspect, the water can include a phosphate-buffered saline solution. In one aspect, the upper chamber can have an open top. In one aspect, the method further includes sealing the open top after the filling. In one aspect, the upper chamber and the lower chamber can have an oval, a circular, a square, a rectangular, or a football cross-sectional shape. In one aspect, the upper chamber can be taller than the lower chamber. In one aspect, the upper chamber can form a closed chamber.

In a second aspect of the disclosure, a method of culturing bone marrow cells is disclosed. The method includes providing a microfluidic device having an upper chamber; a lower chamber; a porous membrane separating the upper chamber from the lower chamber; a first inlet; and a first outlet. The first inlet, the lower chamber, and the first outlet are connected to form a first fluid path through the microfluidic device. A matrix at least partially fills the upper chamber. The matrix includes bone marrow cells. The method further includes flowing a first media through the first fluid path. The first media can include endothelial growth media.

The second aspect can include any one or more of the foregoing aspects, each alone or in any combination. In one aspect, the first media includes endothelial growth media. In one aspect, the endothelial media includes endothelial cell growth media. In one aspect, the endothelial cell growth media includes human microvascular endothelial cells, bovine microvascular cells, fetal-bovine serum, or a combination thereof. In one aspect, the matrix includes an extracellular matrix. In one aspect, the extracellular matrix is fibrin gel. In one aspect, the fibrin gel includes fibrinogen, collagen, aprotinin, thrombin, or a combination thereof. In one aspect, the matrix is a laminin-containing gel. In one aspect, the laminin-containing gel is Matrigel. In one aspect, the matrix is collagen gel. In one aspect, walls of the lower chamber and a bottom surface of the membrane are coated with endothelial cells. In one aspect, the endothelial cells are human umbilical vein endothelial cells. In one aspect, the endothelial cells are human bone marrow endothelial cells. In one aspect, the microfluidic device further includes a second inlet and a second outlet. The second inlet, the upper chamber, and the second outlet are connected to form a second fluid path through the microfluidic device. The method further includes flowing a second media through the second fluid path and over or through the matrix within the upper chamber. The second media includes hematopoietic media. In one aspect, the method further includes collecting one or more samples from effluent from the second outlet. In one aspect, the upper chamber has an open top. In one aspect, the method further includes collecting a sample from the matrix by removing the sample of the matrix through the open top. In one aspect, the open top includes a cover, and the method further includes removing the cover prior to collecting the sample, inserting an instrument through the cover to remove the sample, or a combination thereof. In one aspect, the method includes digesting the sample collected from the matrix with one or more enzymes. In one aspect, the one or more enzymes include nattokinase, collagenase, or a combination thereof. In one aspect, the method includes collecting one or more samples from effluent from the first outlet. In one aspect, the bone marrow cells are bone marrow progenitor cells. In one aspect, the bone marrow progenitor cells are human CD34+ bone marrow progenitor cells. In one aspect, the upper chamber forms a closed channel.

In a third aspect of the disclosure, a method of preparing a bone marrow microfluidic device is disclosed. The method includes providing a microfluidic device having an upper microchannel, a lower microchannel, and a porous membrane separating the upper microchannel from the lower microchannel. The method further includes providing a matrix within the upper microchannel, with the matrix including bone marrow cells. The method further including perfusing a first media through the lower microchannel.

The third aspect can include any one or more of the foregoing aspects, each alone or in any combination. In one aspect, the first media is endothelial media. In one aspect, the endothelial media includes endothelial cell growth media. In one aspect, the endothelial cell growth media includes human microvascular endothelial cells, bovine microvascular cells, fetal-bovine serum, or a combination thereof. In one aspect, the matrix includes an extracellular matrix. In one aspect, the extracellular matrix is fibrin gel. In one aspect, the fibrin gel includes fibrinogen, collagen, aprotinin, and thrombin. In one aspect, the matrix is a laminin-containing gel. In one aspect, the laminin-containing gel is Matrigel. In one aspect, the matrix is collagen gel. In one aspect, the bone marrow cells include stromal cells. In one aspect, the bone marrow cells include bone marrow progenitor cells. In one aspect, the bone marrow progenitor cells include CD34+ bone marrow progenitor cells. In one aspect, the method further includes seeding walls of the lower chamber and a bottom surface of the membrane with endothelial cells. In one aspect, the endothelial cells are human umbilical vein endothelial cells. In one aspect, the endothelial cells are human bone marrow endothelial cells. In one aspect, the method further includes coating the bottom microchannel with fibronectin, collagen, or a combination thereof prior to seeding the first cells. In one aspect, the method further includes flowing a solution of the fibronectin and the collagen through bottom microchannel for about one hour to coat the bottom microchannel. In one aspect, the collagen is collagen type I. In one aspect, the concentration of the fibronectin in the solution is about 100 µg/mL and the concentration of the collagen is about 50 µg/mL. In one aspect, the method further includes rinsing the bottom microchannel with water after the coating. In one aspect, the water includes phosphate-buffered saline solution. In one aspect, the upper microchannel and the lower microchannel have a constant cross-section profile. In one aspect, the upper microchannel forms a closed channel.

In a fourth aspect of the disclosure, a microfluidic device is disclosed that includes an upper chamber having an open top and being partially filled with a matrix including bone marrow cells and a remainder filled with hematopoietic media. The device also includes a lower chamber lined with endothelial cells; a porous membrane that separates the upper chamber from the lower chamber; a first inlet and a first outlet connected to the upper chamber to form a first fluid path; and a second inlet and a second outlet connected to the lower chamber to form a second fluid path.

The fourth aspect can include any one or more of the foregoing aspects, each alone or in any combination. In one aspect, the endothelial cells are human umbilical vein endothelial cells, human bone marrow endothelial cells, or a combination thereof, and the bone marrow cells are bone marrow progenitor cells. In one aspect, the bone marrow progenitor cells are human CD34+ bone marrow progenitor cells. In one aspect, the bone marrow cells include bone marrow stromal cells. In one aspect, the matrix includes fibrin gel composed of fibrinogen, collagen, aprotinin, thrombin, or a combination thereof. In one aspect, the hematopoietic media includes a serum-free expansion medium, fetal bovine serum, cytokines, erythropoietins, a granulocyte colony-stimulating factor, and aprotinin. In one aspect, the endothelial cells are human umbilical vein endothelial cells. In one aspect, the device further includes a removable cover sealing the open top.

In a fifth aspect of the disclosure, a microfluidic device is disclosed that includes an upper microchannel forming a closed channel and being filled with a matrix including bone marrow cells; a lower microchannel lined with endothelial cells; a porous membrane that separates the upper microchannel from the lower microchannel; and an inlet and an outlet connected to the lower chamber to form a fluid path.

The fifth aspect can include any one or more of the foregoing aspects, each alone or in any combination. In one aspect, the endothelial cells are human umbilical vein endothelial cells, human bone marrow endothelial cells, or a combination thereof, and the bone marrow cells are bone marrow progenitor cells. In one aspect, the bone marrow progenitor cells are human CD34+ bone marrow progenitor cells. In one aspect, the bone marrow cells include bone marrow stromal cells. In one aspect, the matrix is fibrin gel comprised of fibrinogen, collagen, aprotinin, thrombin, or a combination thereof. In one aspect, the hematopoietic media comprises a serum-free expansion medium, fetal bovine serum, cytokines, erythropoietins, a granulocyte colony-stimulating factor, and aprotinin.

Additional aspects of the present disclosure will be apparent to those of ordinary skill in the art in view of the detailed description of various embodiments, which is made with reference to the drawings, a brief description of which is provided below.

BRIEF DESCRIPTION OF THE DRAWINGS

FIG. 4A illustrates a top view of another open-top microfluidic device according to aspects of the present disclosure.

FIG. 4B illustrates a cross-sectional view of the open-top microfluidic device of FIG. 4A along the line 4B-4B according to aspects of the present disclosure.

FIG. 4C illustrates a cross-sectional view of the open-top microfluidic device of FIG. 4A along the line 4C-4C according to aspects of the present disclosure.

FIG. 8A shows bone marrow microfluidic device models of acute dose-dependent toxicity at physiologic doses of radiation for an experimental design according to aspects of the present disclosure.

FIG. 8B shows the total cell numbers for devices from FIG. 8A cultured for two weeks, with no radiation (0 Gy) versus 1 Gy versus 4 Gy of radiation given at day 10 according to aspects of the present disclosure.

FIG. 8C shows the quantification of neutrophil and erythroid lineage cells present in devices at the radiation doses indicated according to aspects of the present disclosure.

FIG. 8D shows the number of CD34+ cells present at the radiation doses indicated according to aspects of the present disclosure.

FIG. 9A shows bone marrow microfluidic device models with partial recovery after radiation according to aspects of the present disclosure.

FIG. 9B shows the total cell numbers in the bone marrow microfluidic device models at indicated time points after 2 Gy of radiation at day 10, where a hematopoietic media was supplemented with at a higher dose of granulocyte colony-stimulating factor (10 ng/mL) according to aspects of the present disclosure.

FIG. 9C shows the numbers of neutrophils and erythroid cells at time points indicated after radiation according to aspects of the present disclosure.

FIG. 9D shows the numbers of CD34+ cells at time points indicated after radiation according to aspects of the present disclosure.

Figure 1:
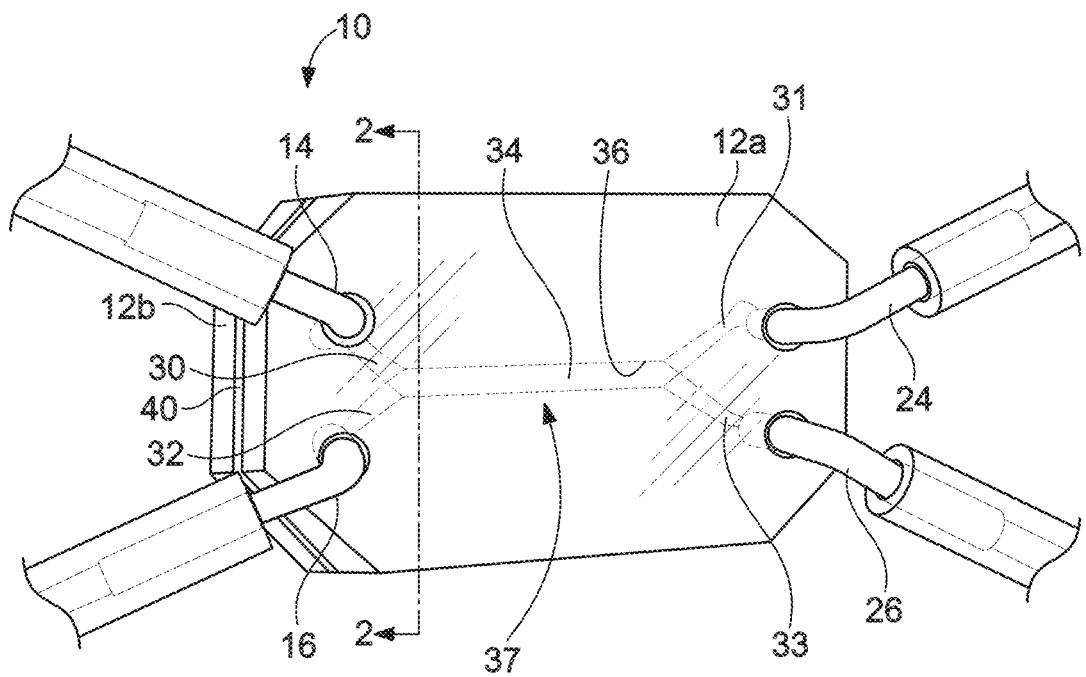
FIG. 1 illustrates an exemplary microfluidic device with a membrane region having cells thereon according to aspects of the present disclosure.

While aspects of the present disclosure are susceptible to various modifications and alternative forms, specific implementations and embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure.

DETAILED DESCRIPTION

While this invention is susceptible of embodiment in many different forms, there is shown in the drawings and will herein be described in detail preferred aspects of the invention with the understanding that the present disclosure is to be considered as an exemplification of the principles of the invention and is not intended to limit the broad aspect of the invention to the embodiment illustrated. For purposes of the present detailed description, the singular includes the plural and vice versa (unless specifically disclaimed); the word "or" shall be both conjunctive and disjunctive; the word "all" means "any and all"; the word "any" means "any and all"; and the word "including" means "including without limitation."

Those of ordinary skill in the art will realize that the following description is illustrative only and is not intended to be in any way limiting. Other embodiments will readily suggest themselves to such skilled persons having the benefit of this disclosure. Reference will now be made in detail to implementations of the example embodiments as illustrated in the accompanying drawings. The same or similar reference indicators will be used throughout the drawings and the following description to refer to the same or like items. It is understood that the phrase "an embodiment" encompasses more than one embodiment and is thus not limited to only one embodiment.

The functionality of cells, tissue types, organs, or organ-components can be implemented in one or more microfluidic devices or "chips" that enable researchers to study these cells, tissue types, organs, or organ-components outside of the body while mimicking much of the stimuli and environment found in vivo. In some aspects, it is desirable to implement these microfluidic devices into interconnected components that can simulate groups of organs, organ-components, tissue systems, and/or other biological systems or environments.

Microfluidic devices formed of microchannels separated by a membrane can be used to model these groups of organs, organ-components, tissue systems, and/or other biological systems or environment. Open-top-style microfluidic devices allow topical access to one or more parts of the device or cells that it comprises. For example, open-top-style microfluidic devices can include a removable cover that, when removed, provides access to the cells of interest in the microfluidic device. The open-top-style systems provide for versatile experimentation when using microfluidic devices.

The present disclosure additionally relates to organ-on-chips ("OOCs"), such as fluidic devices comprising one or more cell types for the simulation one or more of the function of organs, organ-components, and other biological environments and/or systems. Without limitation, specific examples include models of bone marrow found in vivo.

The present disclosure includes fluidic systems that include a microfluidic device with an opening that provides direct access to device regions or components (e.g., access to the gel region, access to one or more cellular components, etc.). Although the present disclosure provides an embodiment wherein the opening is at the top of the device (referred to herein with the term "open top"), the present disclosure contemplates other embodiments where the opening is in another position on the device. For example, in one or more embodiments, the opening is on the bottom of the device. In one or more embodiments, the opening is on one or more of the sides of the device. In one or more embodiments, there is a combination of openings (e.g., top and sides, top and bottom, bottom and side, etc.). While detailed discussion of the "open top" embodiment is provided herein, those of ordinary skill in the art will appreciate that many aspects of the "open top" embodiment apply similarly to open-bottom embodiments, as well as open-side embodiments or embodiments with one or more openings in one or more other regions or directions, and combinations thereof. Similarly, the device need not remain "open" throughout its use; rather, as several embodiments described herein illustrate, the device may further comprise a cover, which may be affixed reversibly or irreversibly. For example, removal of a removable cover creates an opening, while placement of the cover back on the device closes the device. The opening, and in particular the opening at the top, provides a number of advantages, for example, allowing (i) the creation of one or more gel layers for simulating the application of topical treatments on the cells, tissues, or organs, or (ii) the addition of chemical or biological components, such as the seeding of additional cell types for simulated tissue and organ systems.

In some embodiments, one or more of the devices further comprises a gel in a chamber (e.g., cavity) accessible through an opening, including but not limited to an open-top structure, of the microfluidic device. In some embodiments, the device further comprises a removable or permanent cover for the microfluidic device where the cover optionally has a fluidic chamber or microchannel therein.

The present disclosure further describes a method for culturing cells in devices. In some embodiments, the method comprises placing a gel into a chamber. The chamber can be an open-top-style chamber or the chamber can be an enclosed (i.e., non-open-top-style chamber, but otherwise accessible through one or more inlet/outlet ports).

The present disclosure further relates to the use of fluidic systems that include a fluidic device, such as a microfluidic device with an open top, to construct a model simulating the structure and/or one or more functions of, for example, bone marrow. In some embodiments, these models benefit from the presence of gels, which for example, can provide a mechanical and/or biochemical environment for one or more cell types, augment the mass-transport characteristics, and/or provide an additional compartment that may be used, for example, to house an additional cell types.

Figure 2:
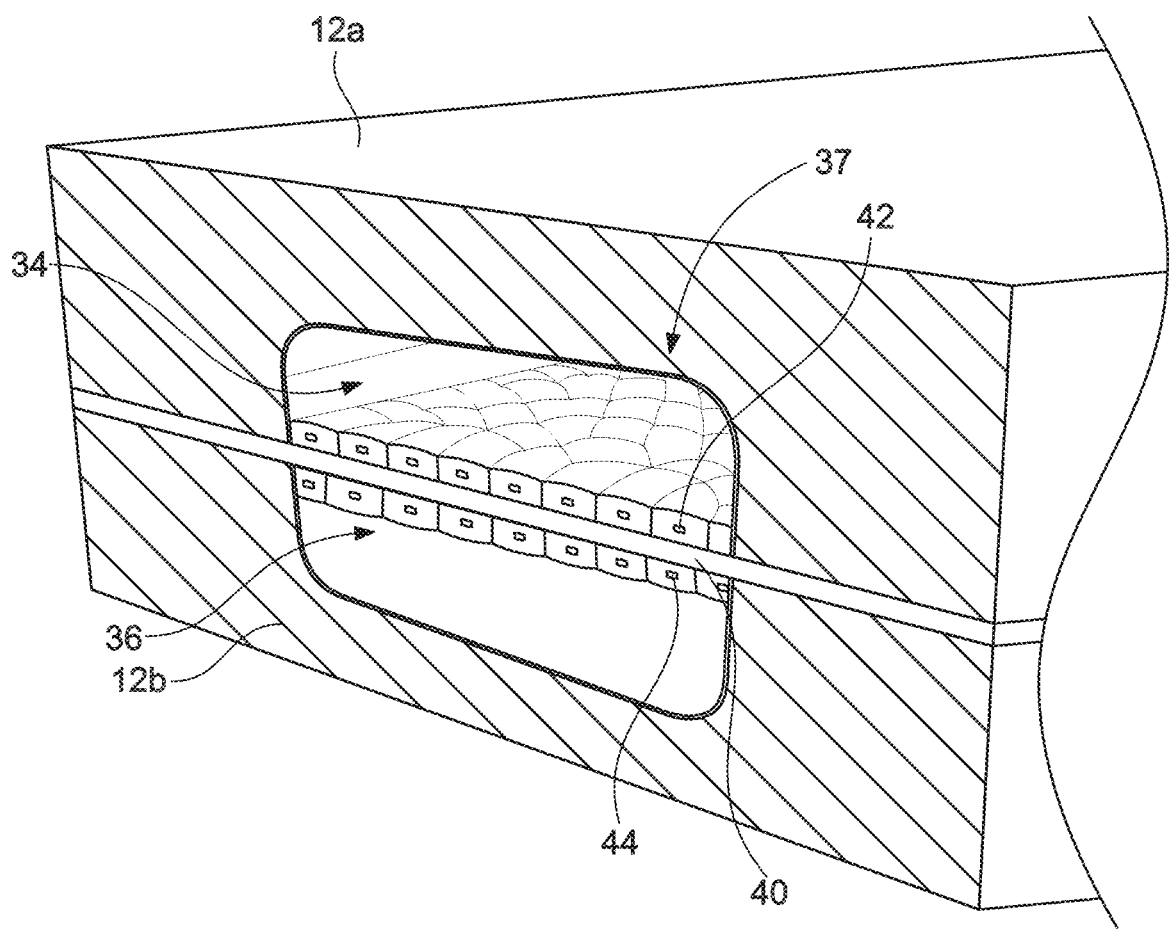
FIG. 2 is a cross-section of the microfluidic device of FIG. 1 taken along line 2-2 according to aspects of the present disclosure.

Referring now to FIGS. 1 and 2, one type of a microfluidic device referred to as an organ-on-chip ("OOC") device 10 is illustrated according to aspects of the present disclosure. As further described below, the microfluidic device of FIGS. 1 and 2 can be modified to include open-top aspects (FIGS. 3-5A). The OOC device 10 includes a body 12 that typically comprises an upper body segment 12a and a lower body segment 12b. The upper body segment 12a and the lower body segment 12b are typically made of a polymeric material, such as PDMS (poly-dimethylsiloxane), polycarbonate, polyethylene terephthalate, polystyrene, polypropylene, cyclo-olefin polymers, polyurethanes, fluoropolymers, styrene derivatives like SEBS (Styrene Ethylene Butylene Styrene), or other polymer materials. The upper body segment 12a, while illustrated with a first fluid inlet 14 and a second fluid inlet 16, can be modified to include an opened region (not shown) to optionally allow the application of a gel layer or other material (not shown) to a membrane 40 and, optionally, modified to exclude the illustrated first fluid inlet 14 and/or second fluid inlet 16. Alternatively, in one or more embodiments, the upper body segment 12a can include different illustrated first fluid inlet 14 and second fluid inlet 16, such as the inlets 14 and 16 coming in from the side (rather than the top).

A first fluid path for a first fluid includes the first fluid inlet 14, a first seeding channel 30, an upper microchannel 34, an exit channel 31, and then the first fluid outlet 24. A second fluid path for a second fluid includes the second fluid inlet 16, a first seeding channel 32, a lower microchannel 36, an outlet channel 33, and then the second fluid outlet 26.

Referring to FIG. 2, a membrane 40 extends between the upper body segment 12a and the lower body segment 12b. The membrane 40 is preferably an inert, polymeric, micro-molded membrane having uniformly distributed pores with sizes in the range of about 0.1 μm to 20 μm, though other pore sizes are also contemplated, as discussed herein. The overall dimensions of the membrane 40 include any size that is compatible with or otherwise based on the dimensions of segments 12a and 12b, such as about 0.05 mm to about 100 mm (channel width) by about 0.5 mm to about 300 mm (channel length), though other overall dimensions are also contemplated. In some aspects, the overall dimensions of the membrane are about 1 mm to about 100 mm (channel width) by about 1 mm to about 100 mm (channel length). The thickness of the membrane 40 is generally in the range of about 5 μm to about 500 μm, and in some aspects, the thickness is about 20 μm to about 50 μm. In some aspects, the thickness can be less than 1 μm or greater than 500 μm. It is contemplated that the membrane 40 can be made of PDMS (poly-dimethylsiloxane), polycarbonate, polyethylene terephthalate, styrene derivatives like SEBS (styrene ethylene butylene styrene), fluoropolymers, or other elastomeric or rigid materials. Additionally, the membrane 40 can be made of biological materials such as polylactic acid, collagen, gelatin, cellulose and its derivatives, poly(lactic-co-glycolic acid), or comprise such materials in addition to one or more polymeric materials. The membrane 40 separates an upper chamber from a lower chamber, such as the upper microchannel 34 from the lower microchannel 36 in an active region 37. The active region 37 can include one or more layers of cells, such as the bilayer of cells 42 and 44 in the illustrated embodiment. In some embodiments, a first cell layer 42 is adhered to a first side of the membrane 40, and in some aspects a second cell layer 44 is adhered to a second side of the membrane 40. The first cell layer 42 may include the same type of cells as the second cell layer 44. Or, the first cell layer 42 may include a different type of cell than the second cell layer 44. And, while a single layer of cells is shown for the first cell layer 42 and the second cell layer 44, either the first cell layer 42, the second cell layer 44, or both may include multiple cell layers or cells in a non-layer structure. Further, while the illustrated embodiment includes a bilayer of cells on the membrane 40, the membrane 40 may include only cells disposed on one of its sides. Furthermore, while the illustrated embodiment includes cells adherent to the membrane 40, cells on one or both sides may instead be not be adherent to the membrane 40 as drawn; rather, cells may be adherent on the opposing chamber surface or embedded in a substrate. In some embodiments, the said substrate may be a gel.

The device 10 is configured to simulate a biological function that typically includes cellular communication between the first cell layer 42 and the second cell layer 44, or between the top microchannel 34 and the bottom microchannel 36, as would be experienced in vivo within organs, tissues, cells, biological systems or environments, etc. Depending on the application, the membrane 40 is designed to have a porosity to permit the migration of cells, particulates, media, proteins, chemicals, and/or other matter between the upper microchannel 34 and the lower microchannel 36. The working fluids or media within the microchannels 34, 36 may be the same fluid or different fluids. As another example, when developing the cell layers 42 and 44 on the membrane 40, the working fluids may be a tissue-culturing fluid. It is contemplated that the device 10 offers utility even in the absence of cells on one side of the membrane 40, as the independent perfusion on either side of the membrane 40 can serve to better simulate mass-transport, shear forces, and other aspects of the biological environment.

In one aspect, the active region 37 defined by the upper and lower microchannels 34, 36 has a length of about 0.1 cm to about 10 cm, and a width of about 10 μm to about 2000 μm. The OOC device 10 can include an optical window that permits viewing of the matter as it moves across the first cell layer 42 and the second cell layer 44. Various image-gathering techniques, such as spectroscopy and microscopy, can be used to quantify and evaluate the effects of the fluid flow in the microchannels 34, 36, as well as cellular behavior and cellular communication through the membrane 40. More details on the OOC device 10 can be found in, for example, U.S. Pat. No. 8,647,861, which is incorporated by reference in its entirety. Consistent with the disclosure in U.S. Pat. No. 8,647,861, in one preferred aspect, the membrane 40 is capable of stretching and expanding in one or more planes to simulate the physiological effects of expansion and contraction forces that are commonly experienced by cells.

Microfluidic and mesofluidic devices and membranes can be fabricated from or coated with or otherwise produced from a variety of materials, including plastics, glass, silicones, biological materials (e.g., gelatin, collagen, fibronectin, laminin, Matrigel®, chitosan, and others).

Figure 3:
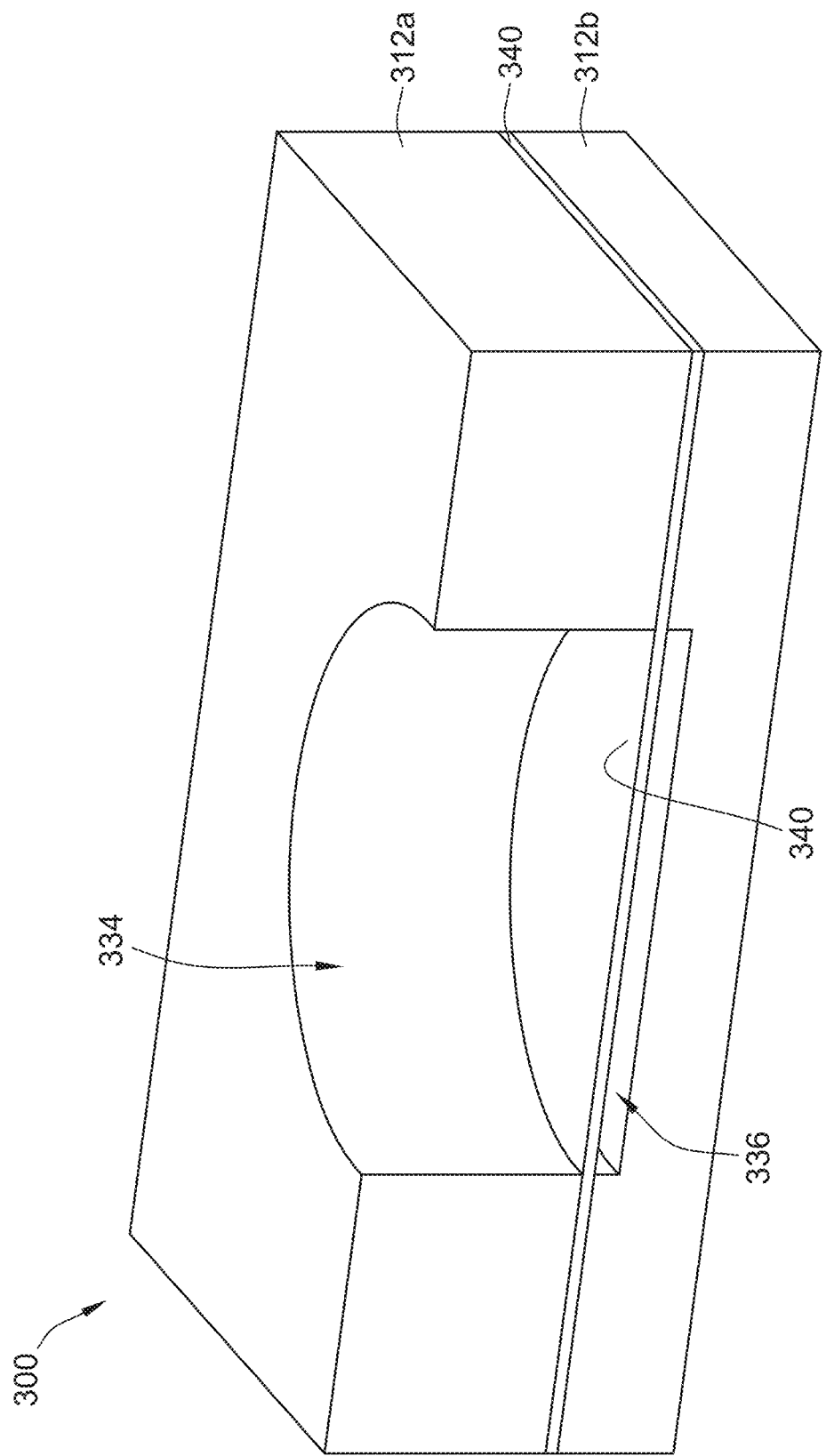
FIG. 3 illustrates an exploded perspective view of an exemplary cross-section through an open-top microfluidic device according to aspects of the present disclosure.
Figure 4D:
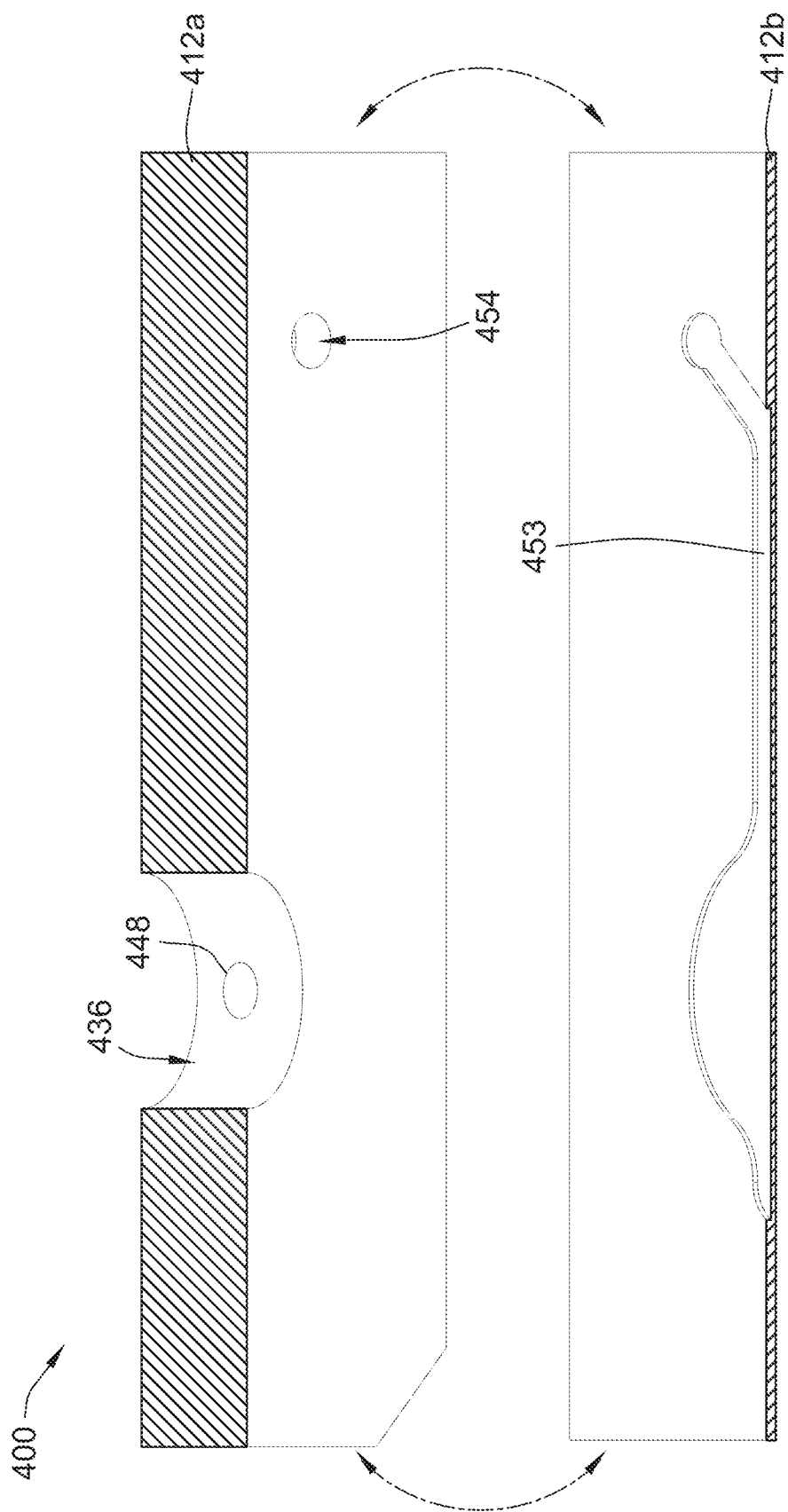
FIG. 4D illustrates a cross-sectional view of the open-top microfluidic device of FIG. 4A along the line 4D-4D according to aspects of the present disclosure.
Figure 4E:
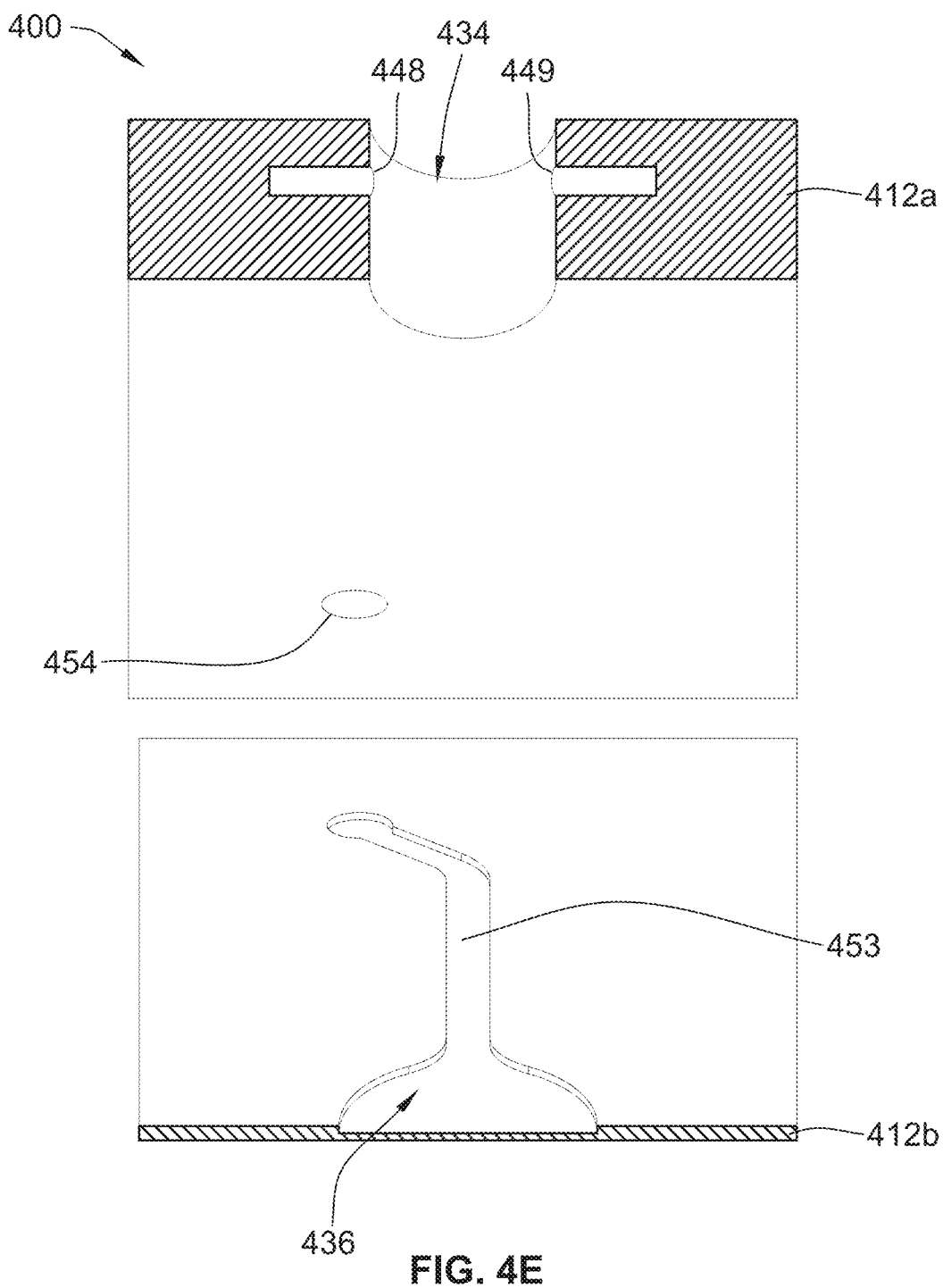
FIG. 4E illustrates a cross-sectional view of the open-top microfluidic device of FIG. 4A along the line 4E-4E according to aspects of the present disclosure.

Referring now to FIG. 3, illustrated is a partial cross-sectional perspective view of an exemplary open-top microfluidic device 300, which is a modified version of the microfluidic device 10 of FIGS. 1 and 2. Similar to the microfluidic device 10, the microfluidic device 300 includes a membrane 340 disposed between a lower body segment 312b and an upper body segment 312a. The lower body segment 312b defines a bottom chamber 336 and the upper body segment 312a defines a top chamber 334. As shown, the top chamber 334 is open at the top so as to define an open region of the microfluidic device 300. As illustrated, the bottom chamber 336 and the open region 334 are generally circular from a top or bottom view perspective. Thus, the bottom chamber 336 and the open region 334 differ, in part, from the microchannels 34 and 36 by having an enlarged cross-section profile as compared to the seeding channels connecting the bottom chamber 336 and the top chamber 334 to the inlets and outlets (described below with respect to FIG. 4A-4E). As a result, the top chamber 334, for example, more closely resembles the interior of a bone where bone marrow is found in vivo than, for example, a microchannel. The shape can vary without departing from the spirit and scope of the present disclosure, such as by having an oval, football, square, rectangular, etc. shape for the open region 334 and/or bottom chamber 336. The illustrated membrane 340 permits migration of cells, particulates, media, proteins, chemicals, and/or other matter between the open region 334 and the bottom chamber 336.

Although not illustrated, the device 300 can include a first fluid path for a first fluid. The first fluid path can include a fluid inlet (similar to the first fluid inlet 14), a seeding channel (similar to the first seeding channel 30), the open region 334, an exit channel (similar to the exit inlet 31), and a fluid outlet (similar to the first fluid outlet 24). The device 300 can also include a second fluid path for a second fluid. The second fluid path can include a fluid inlet (similar the second fluid inlet 16), a seeding channel (similar to the second seeding channel 32), the bottom chamber 336, an outlet channel (similar to the outlet channel 33), and a fluid outlet (similar to the second fluid outlet 26).

In some embodiments, it is desirable that the open region 334 includes a gel, a porous volume, or another material for testing (e.g., an extracellular matrix or cells embedded in an extracellular matrix). For example, a gel can include gels used in an organ-on-chip model of bone marrow, as further described below. Thus, a gel layer can be introduced into the open region 334 such that the gel layer is bounded on the bottom by the membrane 340 and bounded on the side by the upper body segment 312a. In some embodiments, the gel or porous volume is formed by injecting one or more suitable precursors through one or more fluid channels included in the upper body segment 312a. Alternatively, the one of more precursors can be placed into the top of the open-top microfluidic device via the open region 334. In other embodiments, the one or more precursors may be injected into the open region 334 by means of a cover that includes one or more fluidic channels.

In some embodiments, it may be desirable to limit or shape the gel volume or porous volume. For example, in an organ-on-chip model of bone marrow, it is may be desirable to limit the thickness of a gel layer housing to a selected thickness. Without limitation, such thickness may be chosen from one or more of the ranges of about 10 μm to about 200 μm, about 100 μm to about 1 mm, about 0.5 mm to about 5 mm, or about 1 mm to about 10 mm. The overall dimensions of the device can vary. In one or more embodiments, device 300 can have a width of about 5.5 mm and a height of about 5 mm. The bottom chamber 336 can have a width of about 500 μm and a height of about 300 μm. The open region 334 can have a culture area of about 33 mm². The membrane 340 that separates the upper body segment 312a from the lower body segment 312b can have pores of about 7 μm in diameter that are spaced about 40 μm apart. As described above, the membrane 340 can be formed of PDMS about 50 μm thick.

However, in one or more embodiments, the sizes and dimensions can vary. For example, in some aspects, the dimensions of the top area of an open region in an upper body segment for a device can range from about 0.1 mm to about 17 mm along in the narrow dimension. In some aspects, the dimensions range from about 0.5 mm to about 200 mm or more. The lower end of the range of the narrow dimension of the open region is also desirably sized to allow accessibility to the region for pipettes or syringes that are used to place, for example cell cultures or gel materials. The open region can be sized to limit any capillary action, which may be undesirable in some applications (capillary action may nevertheless be desirable in other applications). It is further desirable in some applications for the upper range of the open region dimensions to be sized to maintain accuracy in the flow distribution for the bottom channel across the cell culture area.

In some aspects, the depth of the open region (e.g., measuring vertically upward in the open region from the interface of the top structure with the membrane) can vary from about 0.1 mm to about 20 mm. In some aspects, an additional well or spacer may be added to increase the well volume of the open region, such as where the full depth of the open region is completely filled. It is contemplated that aspect ratios of the dimensions for the top area to the depth of the open region in some applications should range from about 1 to above 100, or in some applications from about less than 0.01 to 2.

In some aspects, it is desirable to have different geometries for the open region based on the type of tissue that is subject to experimentation. For example, certain types of tissue, such as skin, are highly contractile during culturing. When placed into high-aspect ratio (e.g., 16 mm by 1 mm) channels, delamination of the tissue can occur along the narrow dimension. However, an open region that has a circular provides radial symmetry that can allow tissue to shrink uniformly and not move out of plane. A wider channel geometry that minimizes edge effects can also be beneficial for other organ systems that may require multiple layers, such as the blood-brain barrier, airways, or digestive tract, because the layers can be more easily formed by the sequential deposition of thin gel or cellular tissue layers, which is difficult to do in closed channels or chambers.

Referring to FIGS. 4A-4E, another exemplary open-top microfluidic device 400 is shown according to aspects of the present disclosure. The device 400 includes an inlet port 452 and an outlet port 454 disposed in the upper body segment 412a. The inlet port 452 extends into the upper body segment 412a and into a seeding channel of the lower body segment 412b. The seeding channel in the lower body segment 412b then extends into the bottom chamber 436 of the lower body segment 412b and to an outlet channel 453 that is connected to the outlet port 454. Thus, the inlet port 452, the outlet port 454, the channels in the lower body segment 412b, and the bottom chamber 436 form a first fluid path through the device 400. The first fluid path permits flow of fluid and other matter (e.g., cells, particulates, media, proteins, chemicals, etc.) through the bottom chamber 436.

The device 400 also includes an inlet port 458 and an outlet port 459 disposed within the upper body segment 412a. The inlet port 458 extends into the upper body segment 412a and connects to a channel 448 within the upper body segment 412a. The channel 448 connects to the open region 434 through an aperture in the wall of the upper body segment 412a that defines the open region 434. The outlet port 459 extends into the upper body segment 312a and connects to a channel 449 within the upper body segment 412a. The channel 449 connects to the open region through an aperture in the wall of the upper body segment 412a that defines the open region 434. Thus, the inlet port 458, the outlet port 459, the channels 448 and 449, and the open region 434 form a second fluid path through the device 400. The second fluid path permits flow of fluid and other matter (e.g., cells, particulates, media, proteins, chemicals, etc.) through the open region 434. The channels 448 and 449 can be arranged within the open region 434 to be above a matrix (e.g., gel) formed within the open region 434 (discussed below). Thus, the channels 448 and 449, and the inlet 458 port and outlet port 459, allow for the flow of media over a gel formed within the open region 434.

The devices of the present disclosure can be used to culture cells from various biological systems found in vivo. For example, the devices of the present disclosure can be used to mimic biological systems associated with bone marrow and its associated environment. However, the concepts of the present disclosure are not limited to only such biological systems and can instead be used for other systems having similar conditions.

For the purpose of using the devices of the present disclosure to mimic bone marrow and its associated biological environment in vivo, and as applied to the device 400 illustrated in FIGS. 4A-4E, the bottom chamber 436 can be coated with one or more components of an extracellular matrix. In one or more embodiments, the one or more components can include, for example, a glycoprotein. In one or more specific embodiments, the glycoprotein can be fibronectin. In one or more embodiments, the one or more components also can include collagen. In one or more specific embodiments, the collagen can be collagen type I. The one or more components can aid in adhering other components onto the side walls of the bottom chamber 436 and the membrane 340. The other components can include, for example, endothelial cells or other cells to have the bottom chamber 436 mimic microvasculature. In one or more specific embodiments, the endothelial cells can be human umbilical vein endothelial cells, human bone marrow endothelial cells, or a combination thereof. Thus, the one or more components can bind to the walls the bottom chamber 436 and/or can the bottom side of the membrane 440. For example, fibronectin and collagen can adhere to the walls of the bottom chamber 436 and the endothelial cells can adhere to the bottom surface of the membrane 440. Alternatively, endothelial cells can adhere to the walls of the bottom chamber 436 and to the bottom side of the membrane 440. However, in one or more embodiments, the bottom chamber 436 exclude cells lining the walls and the bottom surface of the membrane 440. Instead, the bottom chamber 436 can mimic merely a general lumen without cells.

To coat the bottom chamber 436, the one or more components can flow through the bottom chamber 436 through the first path, by flowing the one or more components into the inlet port 452 and out of the outlet port 454. The one or more components can flow through the device 400 using one or more solutions. For example, all of the components can be within a single solution, or each component can be in a separate solution and a separate flowing step. The solution(s) used can vary; however, in one or more embodiments the solution can be a saline solution, such as a phosphate-buffered saline (PBS) solution.

The one or more components can be in the solution or solutions at various different concentrations. The concentration of the fibronectin in the solution can be about 100 μg/mL. The concentration of the collagen in the solution can be about 50 μg/mL. The concentration of the endothelial cells in the solution can be 4 M/mL. However, the concentrations can vary without departing from the scope of the present disclosure and can be tuned to mimic conditions found in vivo, such as to line the bottom chamber 436 with the endothelial cells and other components of the microvasculature found in vivo. Further, the time the solution is flowed through the bottom chamber 436 can vary to adjust the amount of fibronectin, collagen, and/or endothelial cells that adhere to the bottom chamber 436 and bottom surface of the membrane 440. For example, the solution can flow through the bottom chamber 436 for about one hour. Further, after flowing the solution through the bottom chamber 436, the bottom chamber 436 can be washed by flowing water (which optionally can include PBS) through the bottom chamber 436 and then dried.

Similar to the bottom chamber 436, the open region 434 can be filled with one or more components. To mimic bone marrow found in vivo, in one or more embodiments, the open region 434 can be filled with progenitor cells. In one or more embodiments, the progenitor cells can be human CD34+ progenitor cells. In one or more embodiments, the progenitor cells can include stromal cells, such as bone marrow stromal cells.

The number of progenitor cells in the open region 434 can vary. In one or more embodiments, there can be about 10,000 progenitor cells, such as the human CD34+ progenitor cells, within the open region 434. The progenitor cells can be seeded within the open region 434 within a matrix. In one or more embodiments, the matrix can be an extracellular matrix. By way of example, the matrix can be fibrin gel, collagen gel, a laminin-containing gel, or a combination thereof. With respect to fibrin gel as a specific example, the fibrin gel can be used in an amount of about 50 μL. In one or more embodiments, the fibrin gel can be formed of about 5 mg/mL fibrinogen, 0.2 mg/mL collagen type I, about 25 μg/mL aprotinin, and 0.5 U/mL thrombin.

In some aspects, the progenitor cells, such as the human CD34+ progenitor cells, can be isolated for use as disclosed herein by using a CD34 MicroBead Kit by Miltenyi Biotec, which allows for the positive selection of CD34+ hematopoietic stem and progenitor cells in a single step. Further, the CD34+ cells can be isolated from peripheral blood (PBMCs), bone marrow, leukapheresis product, cord blood, and differentiated ES and iPS cell lines. In one or more embodiments, the human CD34+ bone marrow progenitor cells can be isolated from femoral heads of patients undergoing hip replacement surgery. In some aspects, the human CD34+ bone marrow progenitor cells can include hemaotopoietic stem cells (HSCs).

After filling the open region 434 with the progenitor cells within the gel, the material within the open region 434 can be allowed to crosslink. The remaining space within the open region 434 can then be filled with a working solution or media. In one or more embodiments, the media can be a hematopoietic media. For example, the hematopoietic media can include a serum-free expansion medium, fetal bovine serum (e.g., 10%), cytokines (e.g., 100 ng/mL), erythropoietins (e.g., 3 U/mL), granulocyte colony-stimulating factor (e.g., 1 ng/mL), and aprotinin (e.g., 12.5 μg/mL).

With endothelial cells lining the bottom chamber 436 as described above, the bottom chamber 436 mimics bone marrow microvasculature. The lower portion of the open region 434 just above the porous membrane 440 contains the bone marrow CD34+ progenitor cells suspended in a fibrin gel, which mimics bone marrow. Above the fibrin gel within the open region 434 includes space through which a media can flow. In one or more embodiments, hematopoietic media can flow across the fibrin gel to support the growth and differentiation of the hematopoietic cells. The device 400 configured according to the foregoing mimics the biological system of bone marrow in vivo.

After preparing the open region 434 as described, the open region 434 can be covered. The cover can be removable to allow for sampling of the contents within the open region 434 over time. By way of example, the cover can be an adhesive tape, a removable plate, etc. Alternatively, the cover can be permanently fixed.

Figure 5A:
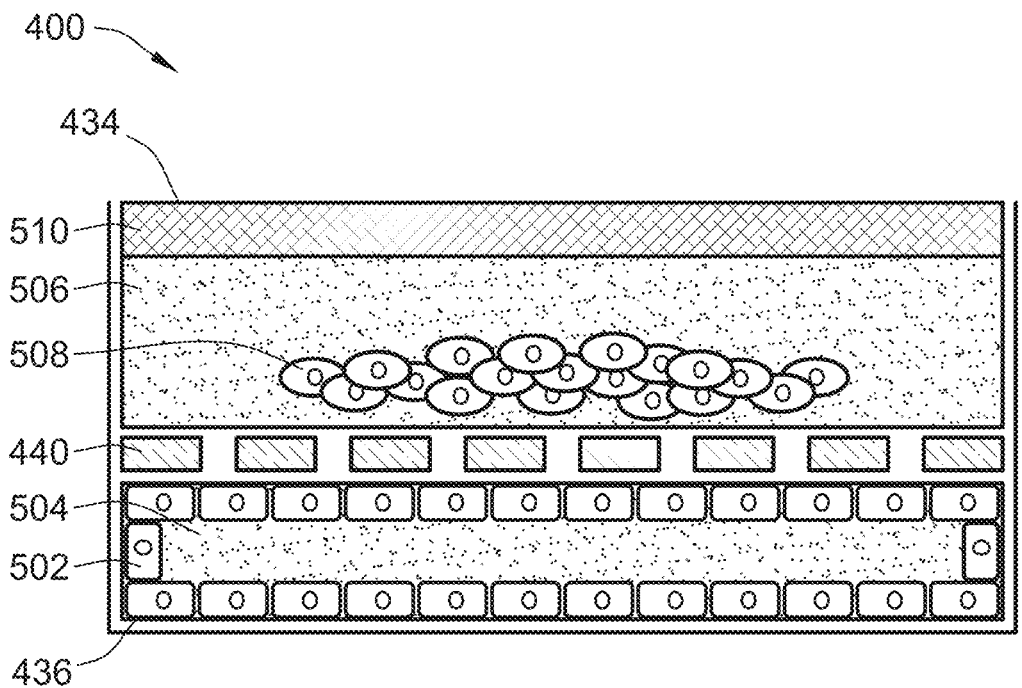
FIG. 5A illustrates a cross-sectional slice of the cells in the open-top microfluidic device of FIG. 4A within the open region according to aspects of the present disclosure.

Referring to FIG. 5A, a cross-sectional slice view of the cells in the open-top microfluidic device of FIG. 4A within the open region 434 is shown according to aspects of the present disclosure. As shown, there is the open region 434 above the membrane 440 and bottom chamber 436. Endothelial cells 502 line the walls of the bottom chamber 436 and the bottom of the membrane. Media 504 can flow through the bottom chamber 436 across the endothelial cells 502. In one or more embodiments, the media 504 can be an endothelial media. By way of example, the endothelial media can be endothelial cell growth media. In one or more embodiments, the endothelial cell growth media can include human microvascular endothelial cells, bovine microvascular cells, fetal bovine serum, or a combination thereof. The top chamber 434 includes the matrix 506 above the membrane 440. In one or more embodiments, the matrix 506 can be an extracellular matrix. By way of example, the matrix 506 can be fibrin gel, a laminin-containing gel, a collagen gel, or a combination thereof. In one or more embodiments, the fibrin gel can include fibrinogen, collagen, aprotinin, thrombin, or a combination thereof. The matrix 506 also includes the bone marrow cells, which can optionally include stromal cells. In one or more embodiments, the bone marrow cells can be bone marrow progenitor cells, such as CD34+ cells. Above the matrix 506 can flow media 510, such as a hematopoietic media. Accordingly, the device 400 allows for the configuration shown in FIG. 5A, which can mimic the biological environment of bone marrow found in vivo.

Figure 5B:
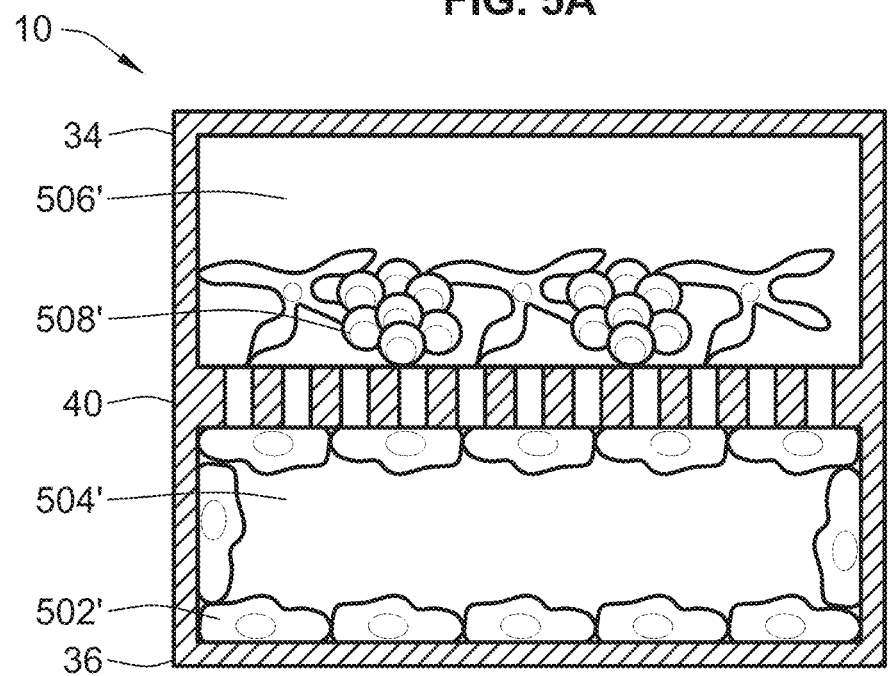
FIG. 5B illustrates a cross-sectional slice of cells in the membrane region of the microfluidic device of FIG. 1 according to aspects of the present disclosure.

Although the device 400 is shown and described primarily in relation to the creating the environment of bone marrow found in vivo, the device 10 can also be used to create a similar environment. Referring to FIG. 5B, a cross-sectional slice view of the cells in the microfluidic device 10 of FIG. 1 is shown, with the device 10 configured as described above with respect to FIGS. 4A-4E, according to aspects of the present disclosure. Endothelial cells 502' line the bottom chamber 36, and media 504' can flow through the bottom chamber 36 past the endothelial cells 502'. Unlike the top chamber 434, which includes the open region, the top chamber 34 is permanently closed and surrounded by fixed walls based on the construction of the device 10. Still, the top chamber 34 includes a gel matrix 506' of CD34+ cells 508' above the membrane 40. Indeed, the top chamber 34 is entirely filled with the matrix 506', which does not allow for the flow of media within the top chamber 34. However, the media 504' still can flow through the bottom chamber 36, and matter (e.g., fluids, cells, particulates, media, proteins, chemicals, etc.) can migrate through the membrane 40 between the top chamber 34 and the bottom chamber 36 and into and out of the media 504'.

Referring back to the device 400 of FIGS. 4A-4E and 5A, with the device 400 prepared according to the foregoing, the device 400 can be connected to a pump, such as a peristaltic pump, to feed media 510 to the open region 434 and media 504 to the bottom chamber 436. As the media 504 and 510 flows through the device 400, samples can be removed from the device 400 from the open region 434, the bottom chamber 436, or a combination thereof. In one or more embodiments, to remove samples from the open region 434, the cover (such as the adhesive tape) can be removed. A sample can then be withdrawn from the exposed open region 434. Alternatively, or in addition, an instrument can be inserted through the cover to remove the sample. In one or more embodiments, the sample can be the supernatant, which can include cells (e.g., CD34+ cells). In one or more embodiments, the samples can be harvested from the media 504 and/or 510 flowing out of the outlet ports 454 and/or 459.

In one or more embodiments, after removal of a sample of the supernatant, the fibrin of the supernatant can be digested with one or more enzymes. By way of example, the one or more enzymes can include nattokinase, collagenase, or a combination thereof. In one embodiment, a solution of 2.5 mg/mL nattokinase and 1 μg/mL collagenase type I in a nutrient medium, such as Dulbecco's Modified Eagle Medium (DMEM) with 10% FBS, can be used to digest the fibrin. Further, in one or more embodiments, a cytology method can be performed to concentrate cells within the sample. By way of example, cytospins can be prepared by centrifuging the cells from the sample in PBS solution with 10% fetal bovine serum.

As a validation of the ability of the microfluidic devices disclosed herein to mimic the conditions and environment of bone marrow found in vivo, tests were performed. The following description and the associated FIGS. 6A-10 validate the ability for the microfluidic devices to mimic bone marrow, and also provide insight into the new types of tests that can be conducted that, prior to the microfluidic devices disclosed herein were not possible.

Figure 6B:
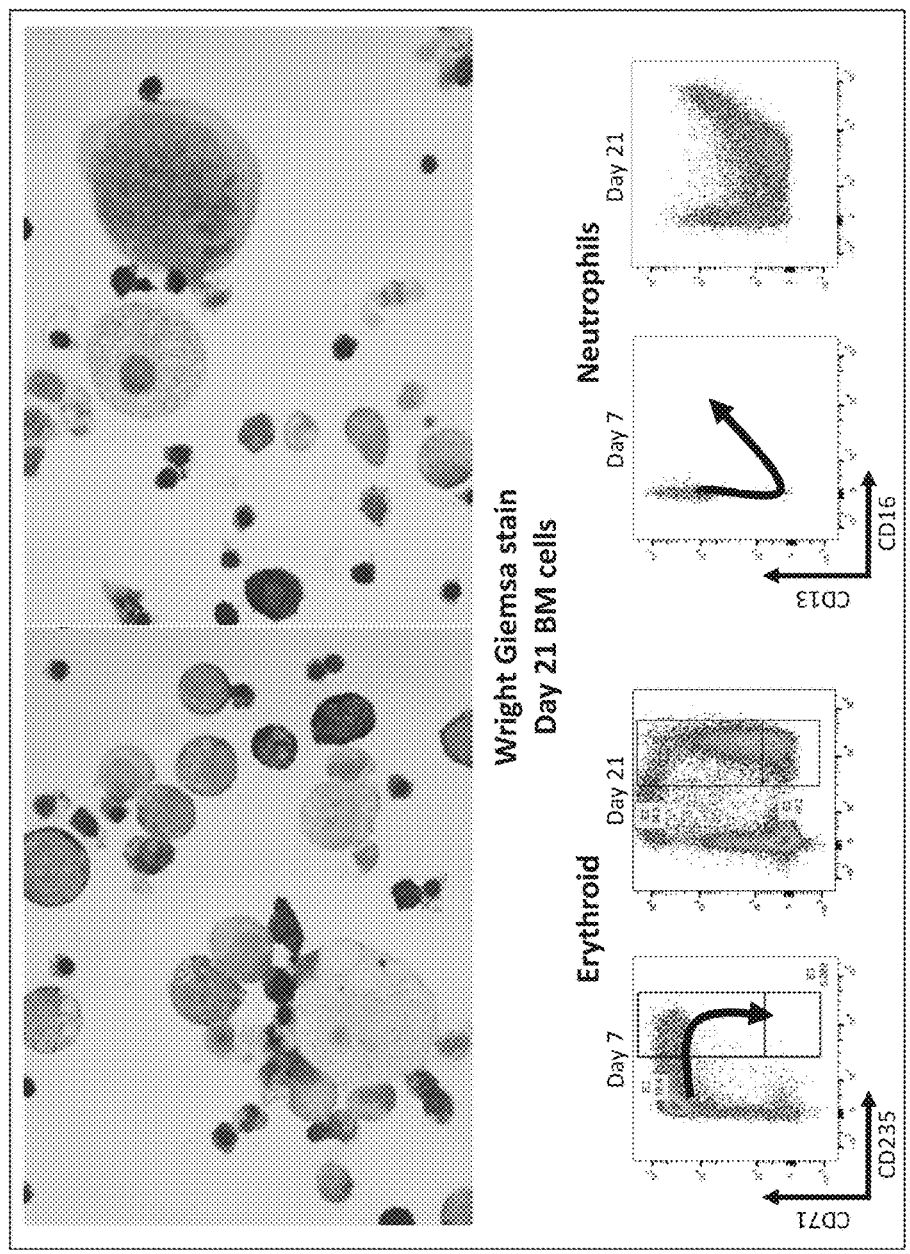
FIG. 6B shows a Wright Giemsa stain of cells from a culture using a microfluidic device according to aspects of the present disclosure.
Figure 6A:
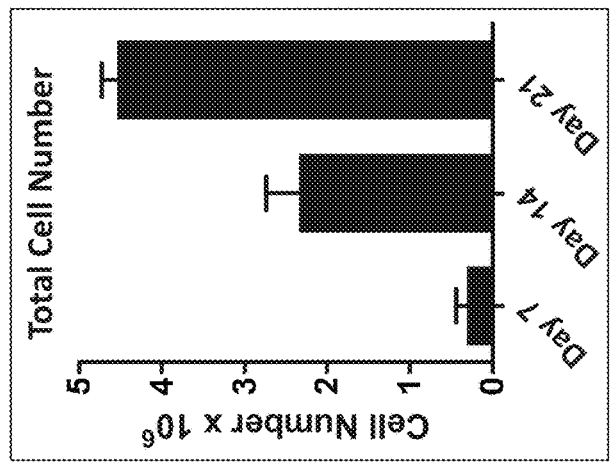
FIG. 6A shows multilineage hematopoiesis with increasing cell numbers in a multi-week hematopoietic culture using a microfluidic chip according to aspects of the present disclosure.

Referring to FIG. 6A, after culturing the device 400 configured as described above for multiple weeks, the device 400 showed continuous expansion of cells over time. Specifically, the cell numbers continued to increase after Day 7, Day 14, and Day 21. Further, FIG. 6B demonstrates the typical mixture of myeloid and erythroid cells present in the device 400 after 21 days of culture. The arrows in the figures illustrate the direction of maturation. Flow cytometry showed that erythroid and neutrophil lineages displayed maturation patterns seen in normal hematopoiesis as assessed by surface marker staining.

Figure 7B:
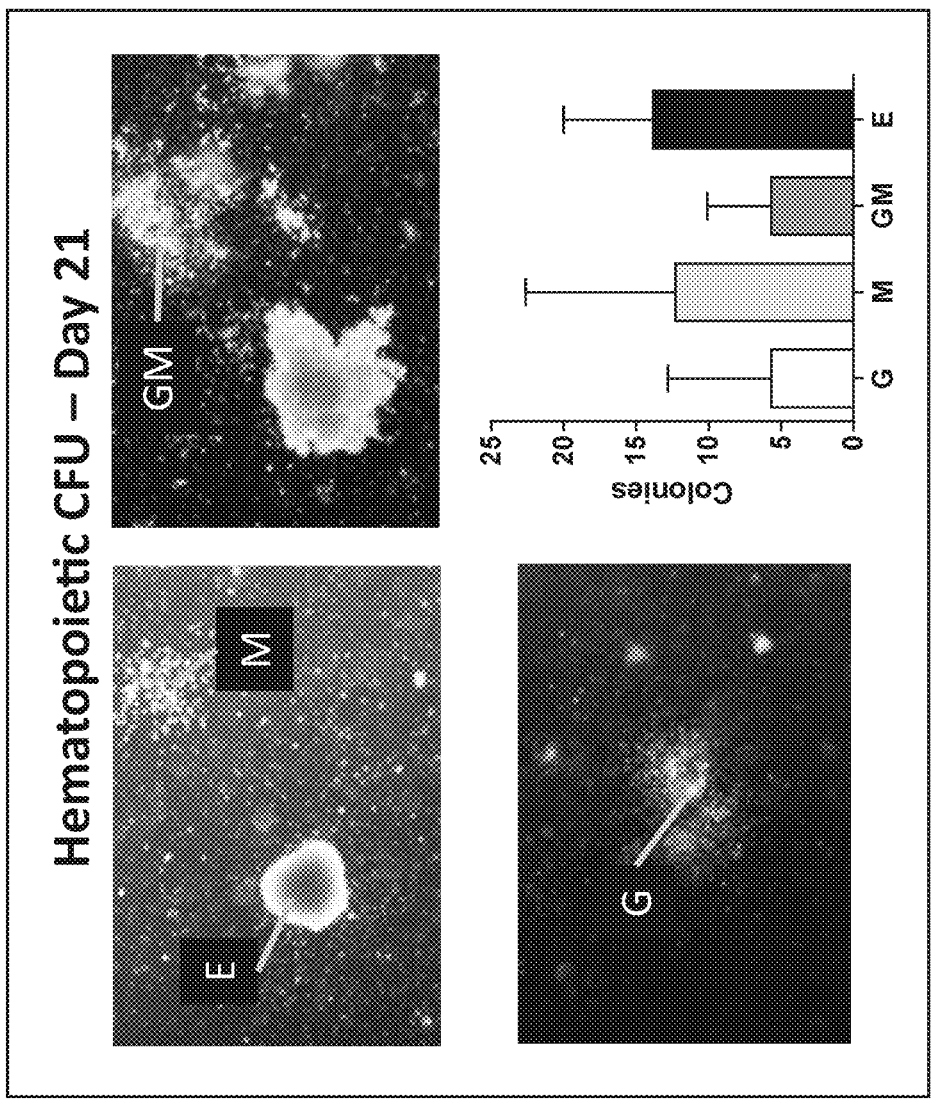
FIG. 7B shows cells harvested from a bone marrow microfluidic device at day 21 to test progenitor function according to aspects of the present disclosure.
Figure 7A:
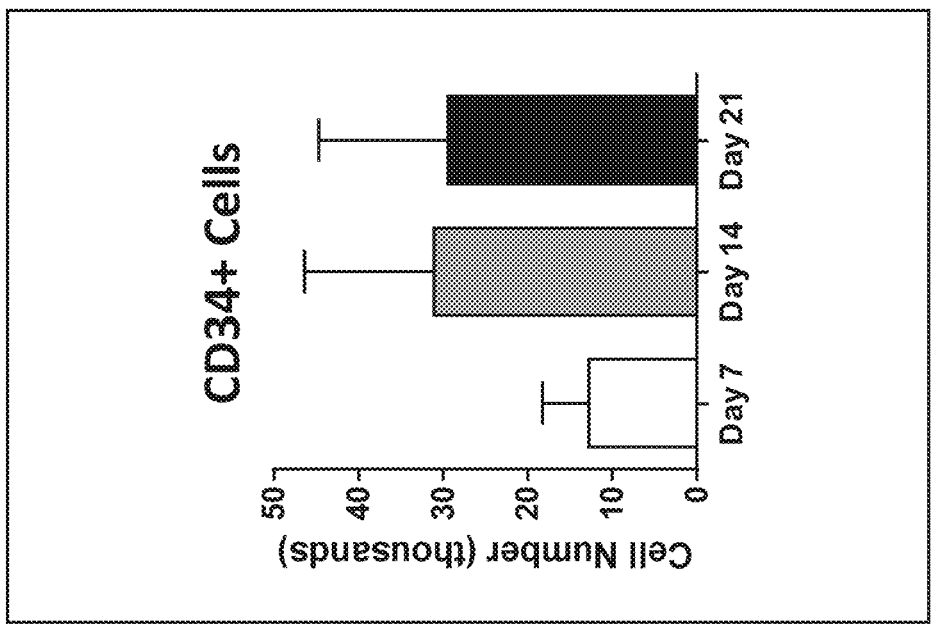
FIG. 7A shows survival and progenitor function of CD34+ bone marrow progenitor cells with the number of CD34+ cells present in a microfluidic device at different times according to aspects of the present disclosure.

Referring to FIG. 7A, as assessed by flow cytometry, the CD34+ cells were still present in the device 400 after multiple weeks of culture, as shown by the amount after Day 7, Day 14, and Day 21. The CD34+ cells harvested from the device 400 at Day 21 were plated in assays to test progenitor function. The CD34+ cells gave rise to myeloid and erythroid colonies in methylcellulose cultures, as shown by the G, M, GM, and E colonies.

Thus, FIGS. 6A through 7B and their associated information validate the ability for the devices and methods disclosed herein to mimic bone marrow environments found in vivo to 21 days after preparing the devices. The results suggest that further growth of the cells is possible beyond the tested periods.

With the ability to mimic bone marrow conditions found in vivo, the devices and methods disclosed herein provide the ability to perform new tests on the microfluidic devices and components therein that were previously not possible. The new tests shed new insight into the bone marrow environment that cannot be learned from other test conditions, such as test conditions found in well plates (discussed below).

Referring to FIG. 8A, to assess the ability of the device 400 to mimic a pathologic process, a challenge with acute myelosuppressive doses of radiation was performed. As shown in FIG. 8A, the device 400 was exposed to the acute myelosuppressive doses of radiation at Day 10. Thereafter, samples were collected and analyzed at Day 14. As a result, the device 400 demonstrated an appropriate dose-dependent response to radiation, showing decreases in multiple cell lineages, neutrophils and erythroids, and loss of CD34+ progenitors, as shown in FIGS. 8B-8D, respectively.

Additionally, the devices and methods disclosed herein allow for various in-vitro models of conditions found in vivo, including a hematopoietic model of radiation recovery. Such a model can have various purposes. In one or more embodiments, such a model can facilitate the search for medical countermeasures to mitigate the myelosuppressive effects of acute gamma radiation exposure.

Referring to FIGS. 9A, long-term culture of the device 400 after exposure to gamma irradiation (e.g., from cesium 137) at Day 10 showed an increase in the total cell numbers from Day 14 to Day 28. This increase indicated at least partial continuation of hematopoiesis. Referring to FIGS. 9B-9D, assessment of neutrophil and erythroid lineages demonstrated that the recovery in cell numbers was largely attributable to an increase in erythroid cells. Further, it was shown that neutrophil and CD34+ cells were not significantly different between days 14 and 28.

Figure 10:
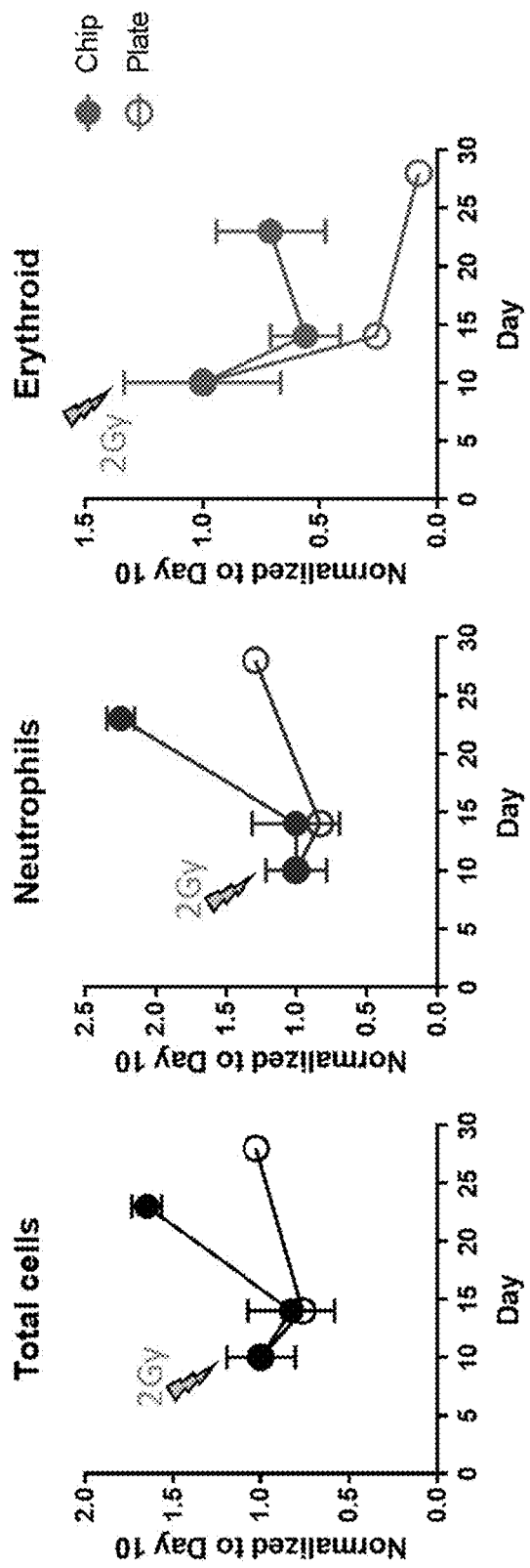
FIG. 10 shows the results of bone marrow microfluidic devices compared to well plate cultures according to aspects of the present disclosure.

As described above, the devices and methods disclosed herein have benefits over previously existing tests based on the ability of the devices to mimic and reproduce conditions. Referring to FIG. 10, results of bone marrow microfluidic devices compared to well plate cultures according to aspects of the present disclosure is shown. To model radiation responses, microfluidic devices 10 versus 96 well plate cultures (containing CD34+ and stromal cells in a fibrin gel) were grown for 10 days and then challenged with 2 Gy of ionizing radiation. After either 4 days or 2-3 weeks later, cells were harvested and analyzed by flow cytometry. The data showed that radiation stopped cell growth in both the microfluidic devices and well plate cultures. However, the microfluidic devices subsequently recovered and resumed robust proliferation, especially in the neutrophil lineage, while the well plate cultures did not. Thus, the microfluidic devices according to the present disclosure, and their associated methods of use, are advantageous for modeling neutrophil recovery responses after myelotoxic stressors such as radiation or drugs, as well as for other purposes related to modeling the bone marrow environment found in vivo. Indeed, previously existing culturing techniques, such as the well plate cultures, were not able to reproduce the same effects.

Unless defined otherwise, all technical and scientific terms used herein have the same meaning as commonly understood by one of ordinary skill in the art to which this invention belongs.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±5%.

Each of the above described aspects and obvious variations thereof are contemplated as falling within the spirit and scope of the claimed invention, which is set forth in the following claims. Moreover, the present concepts expressly include any and all combinations and subcombinations of the preceding elements and aspects.

What is claimed is:

1. A method of preparing a microfluidic device, the method comprising:

providing a microfluidic device having a first microchannel, a second microchannel, and a porous membrane separating the first microchannel from the second microchannel;
providing a matrix within the first microchannel, the matrix comprising CD34+ bone marrow progenitor cells;
perfusing media through the second microchannel;
producing cells differentiated from said CD34+ bone marrow progenitor cells, said differentiated cells comprising erythroid lineage cells.

2. The method of claim 1, wherein the matrix is a fibrin gel.

3. The method of claim 2, wherein said fibrin gel comprises aprotinin.

4. The method of claim 1, further comprising seeding the second microchannel with endothelial cells.

5. The method of claim 1, wherein the first microchannel forms a closed channel.

6. The method of claim 1, wherein said matrix further comprises stromal cells.

7. The method of claim 1, wherein there is no flow of media through said first microchannel.

8. The method of claim 7, wherein media in said second microchannel can migrate through said membrane into said first microchannel.

* * * * *